(12) United States Patent
McMunigal et al.

(10) Patent No.: US 7,771,201 B2
(45) Date of Patent: Aug. 10, 2010

(54) ELECTRICAL RECEPTACLE ASSEMBLY

(75) Inventors: Tom McMunigal, Mead, CO (US);
Jeffrey A. Hammond, Longmont, CO (US); David R. Cooper, Longmont, CO (US)

(73) Assignee: Vivant Medical, Inc., Boulder, CO (US)

( * ) Notice: Subject to any disclaimer, the term of this patent is extended or adjusted under 35 U.S.C. 154(b) by 0 days.

(21) Appl. No.: 12/358,067

(22) Filed: Jan. 22, 2009

(65) Prior Publication Data
US 2009/0130897 A1    May 21, 2009

Related U.S. Application Data

(63) Continuation of application No. 11/899,249, filed on Sep. 5, 2007, now Pat. No. 7,645,142.

(51) Int. Cl.
*H01R 39/00* (2006.01)
(52) U.S. Cl. .......................................................... 439/6
(58) Field of Classification Search .................. 439/11, 439/8, 17, 536, 6, 9, 131, 534–535; 174/67
See application file for complete search history.

(56) References Cited

U.S. PATENT DOCUMENTS

| 5,931,688 | A  | 8/1999 | Hasz et al. |
| 6,379,071 | B1 | 4/2002 | Sorvino |

FOREIGN PATENT DOCUMENTS

| EP | 1732178 | 12/2006 |
| GB | 2128038 | 4/1984 |

OTHER PUBLICATIONS

European Search Report dated Jan. 21, 2009 for European Appln. No. EP 08 01 5204.

*Primary Examiner*—Edwin A. Leon (57) ABSTRACT

A receptacle assembly for use in connecting an energy source to an energy delivering device is described herein. The receptacle assembly includes a face plate defining an aperture. The receptacle also includes an adapter assembly including an adapter plate, supporting a terminal that is operatively connected to the energy source. Additionally, the receptacle includes a spacer member interposed between an inner surface of the aperture of the face plate and an outer surface of the adapter plate, wherein the spacer member permits omni-directional movement of the adapter plate and terminal relative to the face plate.

17 Claims, 8 Drawing Sheets

ELECTRICAL RECEPTACLE ASSEMBLY

CROSS-REFERENCED TO RELATED APPLICATION

This application is a Continuation Application of U.S. patent application Ser. No. 11/899,249 filed on Sep. 5, 2007 now U.S. Pat. No. 7,645,142, the entire contents of is incorporated herein by reference in its entirety.

BACKGROUND

1. Technical Field

The present invention relates to receptacle assemblies and, more particularly, to receptacle assemblies for use in electrical devices, electrosurgical devices, and the like that are especially useful in medical procedures wherein a power source is employed.

2. Description of Related Art

Due to slight part variations, receptacles and the plugs that are designed to connect to the receptacles sometimes do not align perfectly. This can cause the receptacles and the plugs to fail to operate and function as intended, which can cause discontent to the user and damage to the receptacle or plug during connection and/or disconnection. The present disclosure relates to receptacle assemblies that can compensate for misalignment between the receptacle and the plug caused by these slight part variations.

When the receptacle and the plug are misaligned a number of concerns may arise. For example, the force needed to extract and/or insert the plug into the receptacle can be greater than when the receptacle and the plug are properly aligned. In another example, the connection between the receptacle and the plug might be too loose. As a result, the plug may not sit properly within the receptacle or the user may perceive that a proper connection has not been established.

SUMMARY

A receptacle assembly for use in connecting an energy source to an energy delivering device is provided. In one embodiment, the energy source and the energy delivering device may be used to perform a medical procedure using a power source in the RF frequency spectrum.

The receptacle assembly includes a face plate defining an aperture, an assembly including an adapter late supporting a terminal that is operatively connected to the energy source, and a resilient spacer interposed between an inner surface of the aperture of the face plate and an outer surface of the adapter plate.

The aperture of the face plate is sized and shaped to permit omni-directional movement of the adapter plate, the aperture and the terminal being aligned along a common central axis. In one embodiment, the face plate is removably attached to the energy source. The face plate includes a connector that extends from a front surface of the face plate to a rear surface of the face plate. The face plate includes at least two additional apertures that correspond to at least two oversized oval apertures on the adapter plate. The additional apertures on the face plate are configured to each receive a fastening device, wherein the fastening device can be at least two thumbscrews.

In one embodiment, the adapter plate has the terminal permanently attached thereto. In an alternative embodiment, the terminal may be removably secured to the adapter plate such as via a locknut or the like. The adapter plate includes the oversized oval apertures that extend from a front surface of the adapter plate to a rear surface of the adapter plate. The adapter plate also includes an O-ring groove. In one embodiment, the face plate and the adapter plate are adjustably attached to each other.

The resilient spacer interposed between an inner surface of the aperture of the face plate and outer surface of the adapter plate permits omni-directional movement of the adapter plate and terminal relative to the face plate. In one embodiment, the spacer is an O-ring that is in operative contact with the O-ring grove.

DETAILED DESCRIPTION

Detailed embodiments of the present disclosure are described herein; however, it is to be understood that the disclosed embodiments are merely exemplary of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Figure 1:
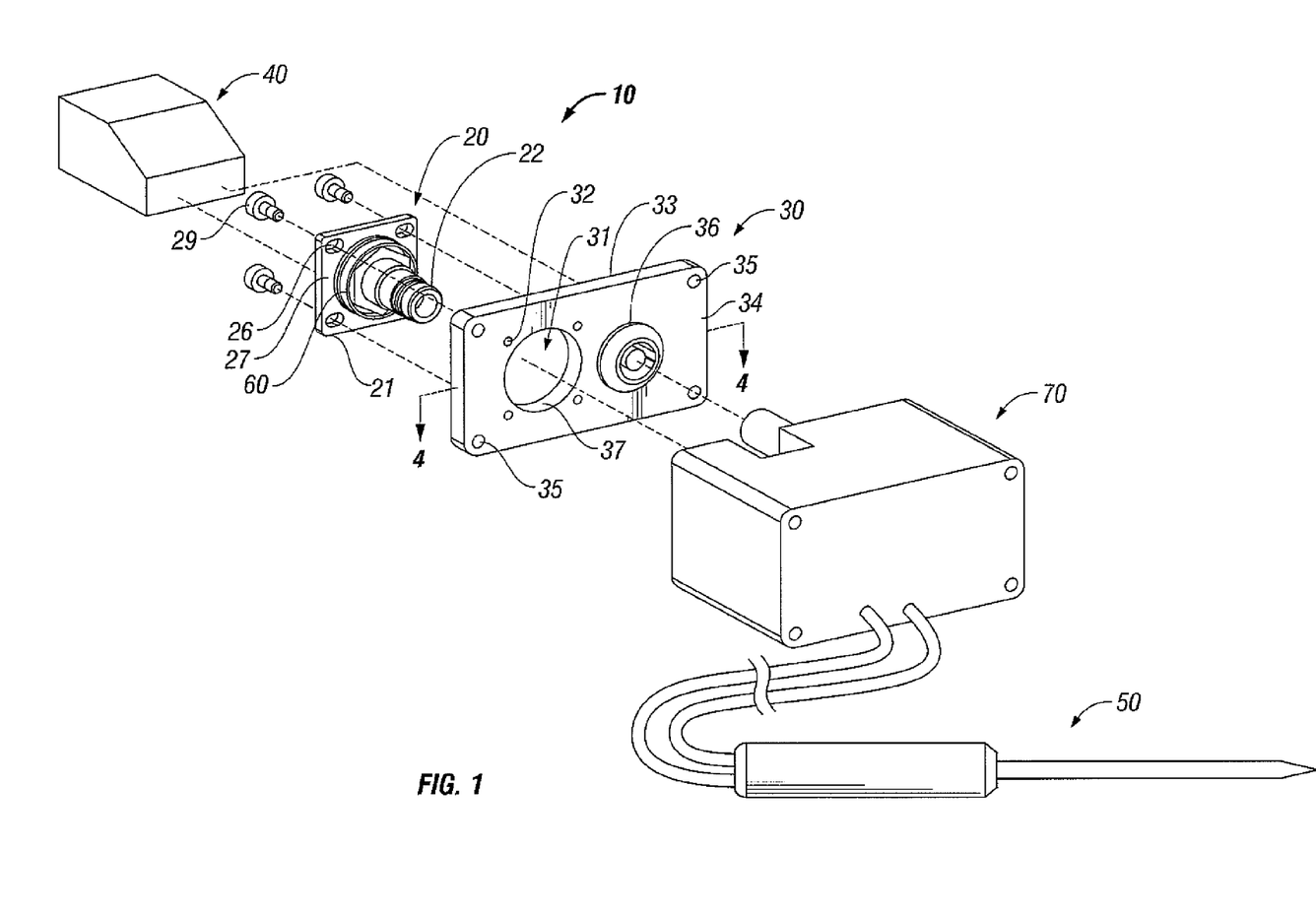
FIG. 1 is a partially exploded perspective view of a receptacle assembly according to one embodiment of the present disclosure, with the adapter assembly and face plate assembly separated from one another.
Figure 4:
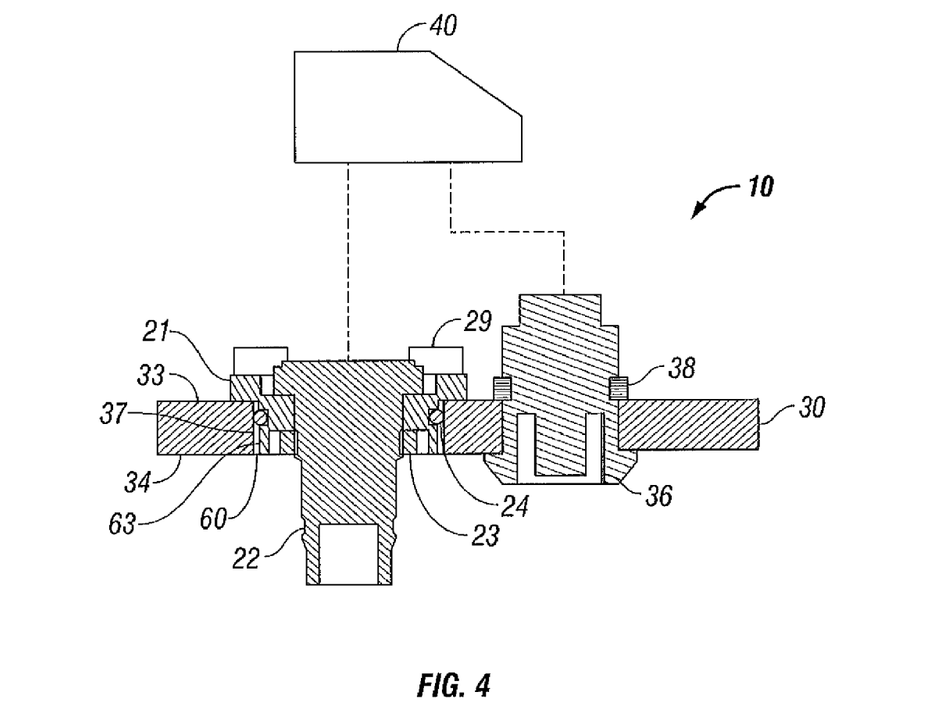
FIG. 4 is a cross-sectional view of the receptacle assembly of FIGS. 1 and 2 as taken through 4-4 of FIG. 1, illustrating a terminal secured to a face plate thereof.

With reference to FIGS. 1 and 4, a receptacle assembly according to an embodiment of the present disclosure is generally designated 10. Receptacle assembly 10 may be used for connecting a suitable energy source 40 to a suitable energy delivering device 50. The energy source 40 and the energy delivering device 50 may be configured to perform an electrosurgical medical procedure using a power source in the RF frequency spectrum from relatively low frequencies (3-30 Megahertz) to relatively high frequencies (30-300 Gigahertz). Other suitable applications are contemplated by the present disclosure.

In the illustrated embodiment receptacle assembly 10 includes an adapter assembly 20 and a face plate 30 configured to support adapter assembly 20. Adapter assembly 20 includes an adapter plate 21 configured to support a plug or terminal 22. Terminal 22 can be configured for operative connection to the energy source 40.

Terminal 22 may be secured to adapter plate 21 via a suitable securing element, such as a locknut 23. Alternatively, as seen in FIGS. 5-8, terminal 22 may be permanently attached to adapter plate 21 via suitable adhesives or the like.

Figure 2:
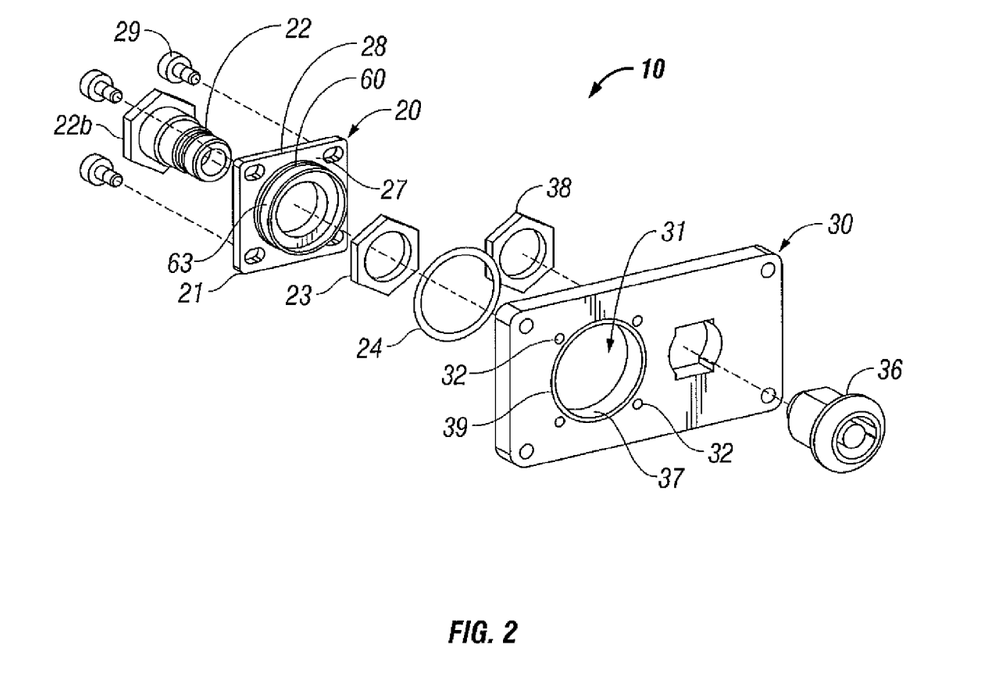
FIG. 2 is an exploded view of the receptacle assembly of FIG. 1.
Figure 3:
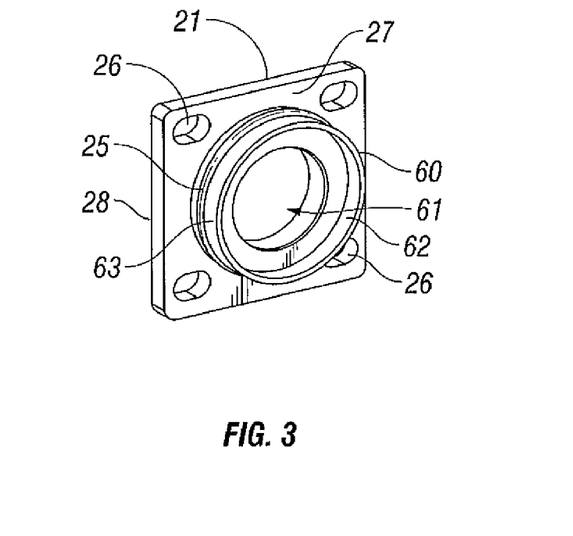
FIG. 3 is an enlarged perspective view of an adapter plate of the receptacle assembly of FIGS. 1 and 2.

As seen in FIGS. 1-3, adapter plate 21 can have any suitable shape including but not limited to polygons (e.g., rectangular), spherical polygons (e.g., circular), and the like. Adapter plate 21 may be defined by a front surface 27, a rear surface 28, and sidewall(s).

Adapter plate 21 includes a flange 60 extending from front surface 27 thereof. The distance that flange 60 extends from front surface 27 will depend on the desires and/or needs of the user. Flange 60 may be sized and shaped to fit within a corresponding bored cavity 39 that can be located on a rear surface 33 of a face plate 30, as seen best in FIGS. 2 and 4. Flange 60 may also be sized and shaped to receive an attaching device 23 for connecting terminal 22 to adapter plate 21.

Flange 60 can be any suitable shape including but not limited to polygons, spherical polygons and the likes. In one embodiment, as seen in FIGS. 2 and 3, flange 60 can have a generally circular shape defined by generally circumferential inner and outer walls, 62 and 63, respectively. Additionally, flange 60 defines an aperture 61 extending through adapter plate 21. Aperture 61 can be configured to receive a portion of terminal 22 therein.

With reference to FIGS. 2 and 3, flange 60 includes a circumferential groove 25 formed in outer wall 63 thereof. Groove 25 is configured to receive a resilient spacer member 24 therein. The exact dimensions of groove 25 may depend on the dimensions of resilient spacer member 24, and this may depend on the desired seal between outer wall 63 of the flange 60 and an inner circumferential surface 37 of aperture 31 of face plate 30.

In the illustrated embodiment, resilient spacer member 24 is an O-ring; however the spacer member employed can be any suitable spacer member known in the available art including a gasket, a bearing, a bushing and the like. It is further contemplated that instead of resilient spacer member 24 being disposed within groove 25 formed in outer wall 63 of flange 60, resilient spacer member 24 can be a located within a circumferential groove (not shown) formed in inner circumferential surface 37 of aperture 31 of face plate 30.

In addition, resilient spacer member 24 can be made from any suitable type of material known in the available art including but not limited to synthetic rubbers and thermoplastics, which may be selected from the group comprising: acrylonitrile butadiene copolymers; butadiene rubber; butyl rubber; chlorosulfonated polyethylene; ethylene propylene diene monomer; ethylene propylene monomer; fluoroelastomers; perfluoroelastomer; polyacrylate; polychloroprene; polyisoprene; polysulfide rubber; semi-conductive fluorocarbon with nano carbon tubes; silicone rubber; styrene butadiene rubber; thermoplastic elastomer styrenics; thermoplastic polyolefin LDPE, HDPE, LLDPE, ULDPE; thermoplastic polyurethane polyether, polyester; thermoplastic etherester-elastomers; copolyesters; thermoplastic polyamide polyamides; melt processible rubber; and thermoplastic vulcanizate.

If needed, an additionally a lubricant, not shown, may be applied to groove 25 and resilient spacer member 24. The lubricant can be employed to facilitate the operability and/or maintainability of resilient spacer member 24.

With specific reference to FIG. 3, adapter plate 21 includes at least two apertures 26 formed therein and extending from front surface 27 to rear surface 28 of adapter plate 21. In addition, the apertures 26 can be located at opposite corners of adapter plate 21. The apertures 26 can be configured to facilitate omni-directional movement of the adapter plate 21. In the illustrated embodiment, adapter plate 21 includes four apertures 26 formed therein each located near a respective corner of adapter plate 21.

Figure 9:
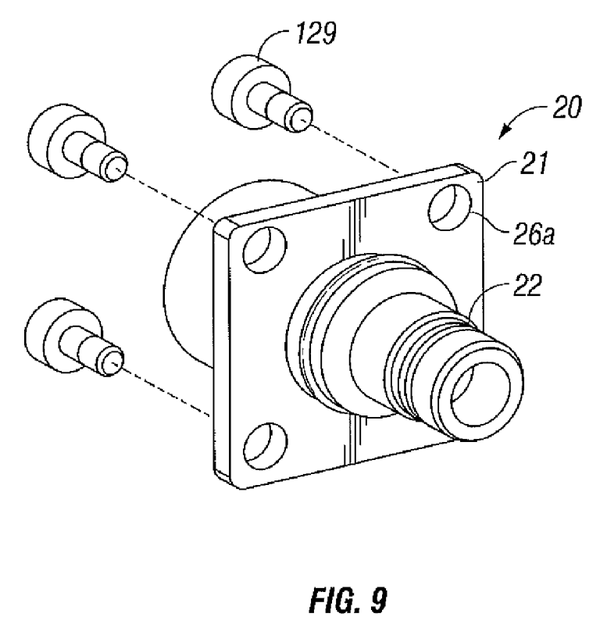
FIG. 9 is an enlarged perspective view of an adapter plate according to another embodiment of the present disclosure.

The apertures 26 can be any suitable shape including circular, oval, square, rectangular and the like. In one embodiment, the apertures 26 are generally oval in shape. For a given thumbscrew head diameter, employing at least two apertures 26 that are generally oval in shape can allow for maximum longitudinal motion of the adapter plate 21. Alternatively, as shown in FIG. 9, each aperture 26a can be generally circular in shape.

Figure 10:
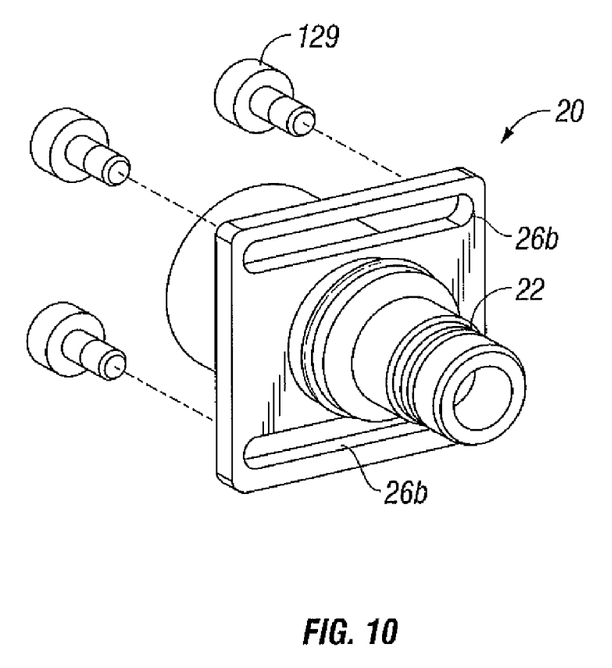
FIG. 10 is an enlarged perspective view of an adapter plate according to yet another embodiment of the present disclosure.

In another embodiment, as seen in FIG. 10, instead of employing at least two apertures 26, there can be at least two generally elongate slots 26b. In this embodiment, the slots 26b extend from the front surface 27 to the rear surface 28. Additionally, the slots can extend substantially from one side to an opposite side of adapter plate 21.

Referring back to FIG. 1, the apertures 26 of adapter plate 21 can be aligned along a common central axis of at least two corresponding apertures 32 formed in face plate 30.

Each aperture 26 can be configured to receive a fastening device 29. Fastening device 29 may be any suitable fastening device, such as a flathead screw, a Philips head screw, shoulder bolt, pin, nut and bolt, and the like.

With reference to FIGS. 1, 2, 5, and 6, adapter plate assembly 20 is configured to selectively support a terminal 22. Terminal 22 may be operatively and selectively connected to the internal circuitry and/or components (not explicitly shown) of energy source 40. For example, in one embodiment, terminal 22 can be configured as part of a male-female connection, wherein the distal end of terminal 22 can have either a male or female configuration. In alternative embodiment, the distal end of terminal 22 can have wires configured to attach to the internal circuitry of energy source 40. Terminal 22 may further include any suitable feature needed for energy source 40 and energy delivering device 50 to function as intended.

Figure 5:
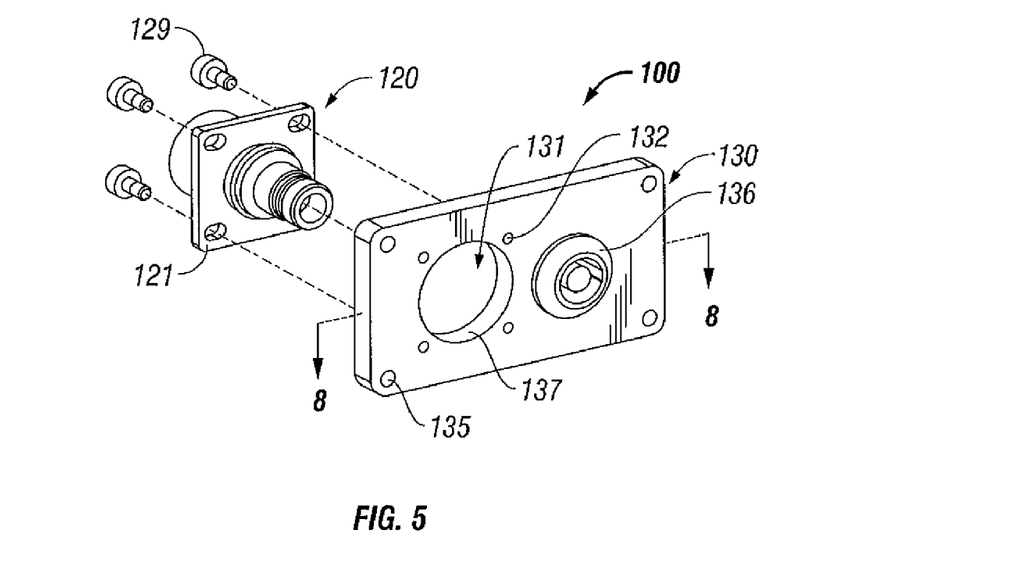
FIG. 5 is a partially exploded perspective view of a receptacle assembly according to another embodiment of the present disclosure, with the adapter plate and face plate separated from one another.
Figure 6:
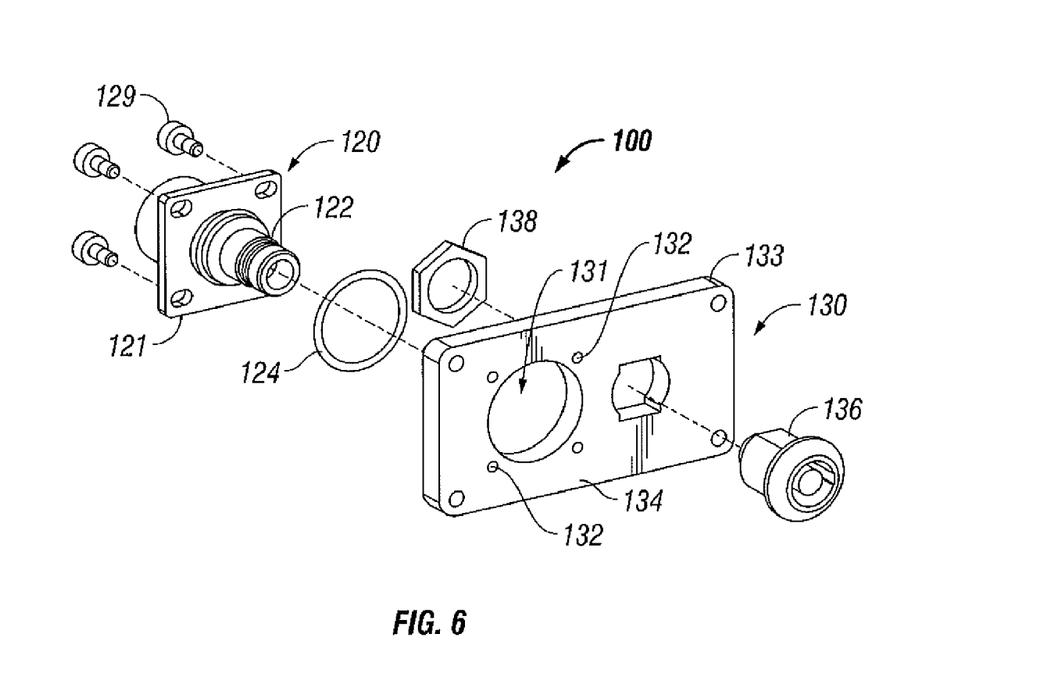
FIG. 6 is an exploded view of the receptacle assembly of FIG. 5.
Figure 7:
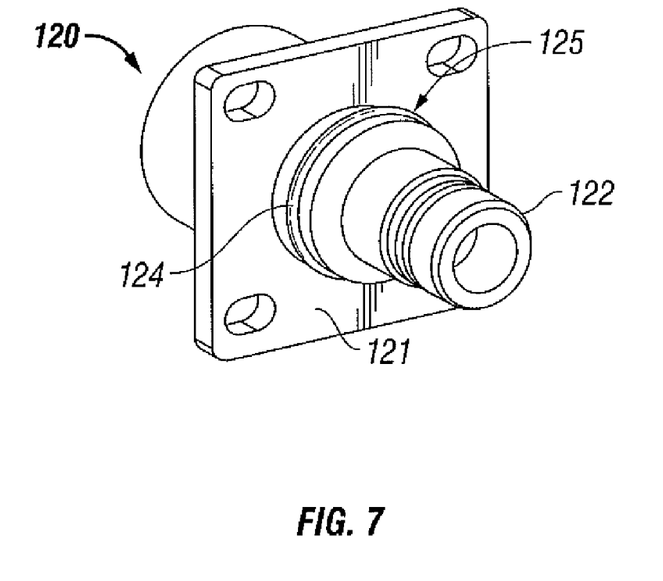
FIG. 7 is an enlarged perspective view of an adapter plate of the receptacle assembly of FIGS. 5 and 6.

In one embodiment, as seen in FIGS. 1, 2 and 4, terminal 22 can be coupled to adapter plate 21 via a locknut 23, wherein terminal 22 can have external threads and locknut 23 can have internal threads, or vice versa. In another embodiment, terminal 22 can be coupled to adapter plate 21 via a traditional screw fit method, wherein terminal 22 can have external threads and adapter plate 21 can have internal threads provided in aperture 62 thereof. In yet another embodiment, terminal 22 can be press fit into adapter plate 21. In still another embodiment, as seen in FIGS. 5 and 6, terminal 22 can be permanently coupled to the adapter plate 21 via adhesives or welding, as will be discussed in more detail below.

As seen in FIGS. 1 and 2, face plate 30 includes at least two apertures 32 formed therein at a location substantially aligned with corresponding apertures 26 of adapter plate 21 when adapter plate 21 is connected to face plate 30. The apertures 32 can be configured to each receive a fastening device 29, such as, for example, thumbscrews. Further, face plate 30 includes an aperture 31 configured to allow for omni-directional movement of adapter plate 21 when adapter plate 21 is attached thereto. Face plate 30 can be removably or fixedly coupled to energy source 40 via suitable fastening members (not shown) extending through apertures 35 formed in face plate 30. Face plate 30 may be configured to support a connector or terminal 36.

With continued reference to FIGS. 1, 2 and 4, face plate 30 can have an aperture 31 formed therein. Aperture 31 can be any suitable shape, such as polygons, spherical polygons and the like. Aperture 31 can be generally circular in shape and defined by a generally inner circumferential wall 37, which can extend from front surface 34 to a rear surface 33 of face plate 30. Aperture 31 of face plate 30 is sized to be larger than flange 60 of adapter plate 21. In this manner, when adapter plate 21 is attached to face plate 30, flange 60 of adapter plate 21 is inserted into aperture 31 of face plate 30 and resilient spacer member 24 of adapter plate 21 is interposed between inner circumferential wall 37 of aperture 31 and outer wall 63 of flange 60.

Figure 8:
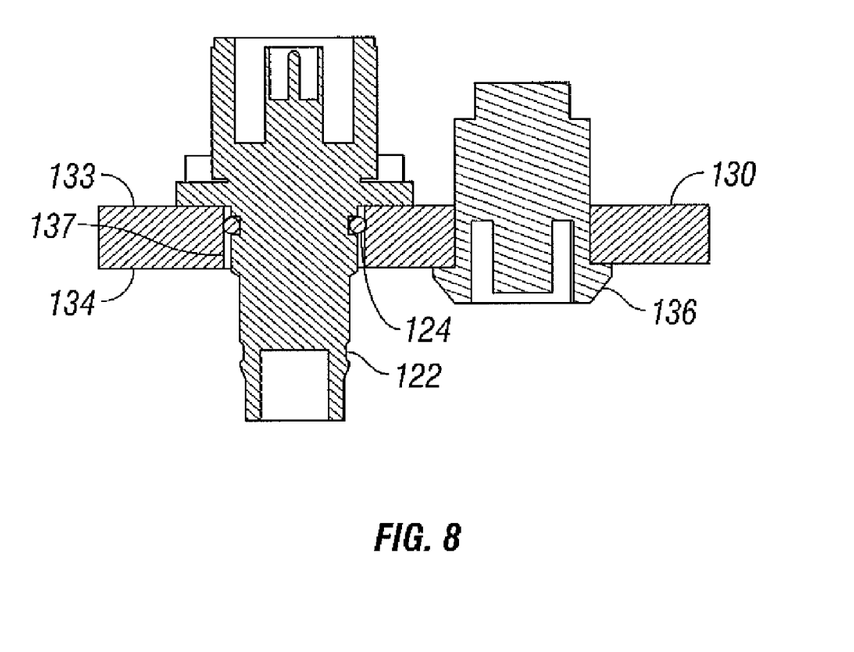
FIG. 8 is a cross-sectional view of the receptacle assembly of FIGS. 5 and 6 as taken through 8-8 of FIG. 5, illustrating a connector secured to a face plate thereof.

Terminal 36 may be any suitable type of terminal known in the available art including but not limited to an electrical connector, an RF connector, an audio connector, a video connector, and the like. In one embodiment, terminal 36 may be a 10 pin connector that may be used for securing a corresponding 10-pin prong. Additionally, terminal 36 may be secured to face plate 30 via any of the aforementioned securing devices and/or methods employed for securing terminal 22 to adapter plate 21. For example, in one embodiment, terminal 36 may be secured to face plate 30 via a locknut 38 (see FIGS. 2 and 4). In another embodiment, as seen in FIG. 8 terminal 36 may be secured to face plate 30 via a press fit.

Further, as seen in FIG. 4, terminal 36 may be connected to the internal components and/or circuitry of energy source 40. For example, in one embodiment, terminal 36 may be configured as part of a male-female connection, wherein the distal end of terminal 36 may have either a male or female configuration. In an alternative embodiment, the rear end of terminal 36 may have wires configured to attach to the internal circuitry of energy source 40. Terminal 36 may include any suitable features needed for energy source 40 and energy delivering device 50 to function and operate as intended.

Turning now to FIGS. 5-8, a receptacle plate assembly according to an alternative embodiment of the present disclosure is hereinafter represented by the reference numeral 100. As shown in FIGS. 5-8, receptacle plate assembly 100 includes an adapter assembly 120 and a face plate 130. Adapter assembly 120 and face plate 130 function in a similar fashion as in the hereinbefore described adapter assembly 20 and face plate 30. As a result, and unless otherwise noted, only the features and/or members that are unique to adapter plate assembly 120 and face plate 130 will be hereinafter discussed.

With continued reference to FIGS. 5-8, adapter assembly 120 includes an adapter plate 121 and a terminal 122 permanently attached thereto as described above. Terminal 122 may be molded or formed as a part of adapter plate 121 or may be permanently attached to adapter plate 121 via soldering, welding, brazing and the like.

As seen in FIGS. 5-10, terminal 122 includes a circumferential groove 125 configured to support or retain a spacer member 124 therein. As so configured, when adapter assembly 120 is secured to face plate 130 via fastener members 129, spacer member 124 is interposed between terminal 122 and an inner circumferential wall 137 of aperture 131 of face plate 130.

Figure 11:
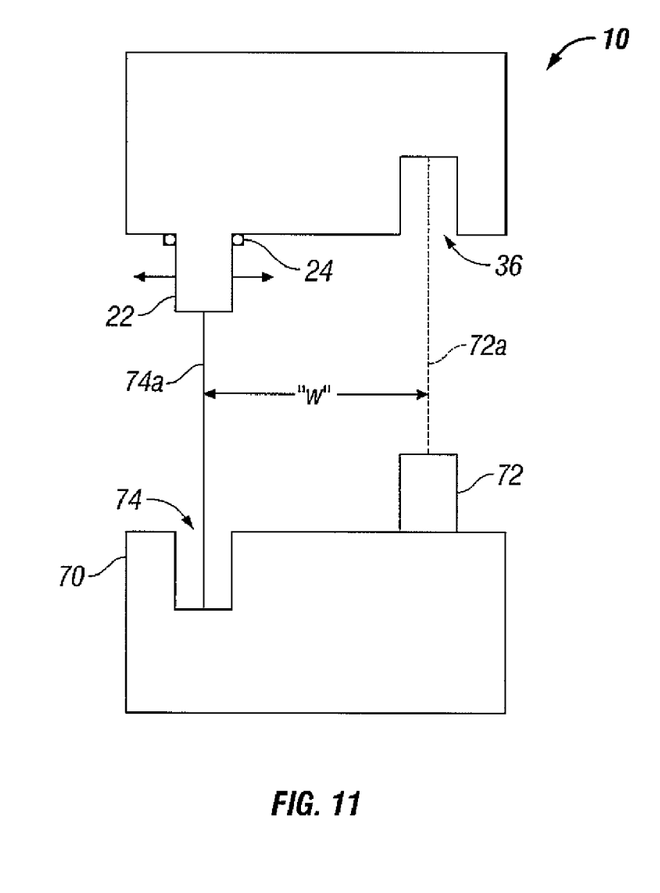
FIG. 11 is a schematic plan view of a receptacle assembly and a plug of an energy delivering device aligned along a common central axis according to one embodiment of the present disclosure.
Figure 12:
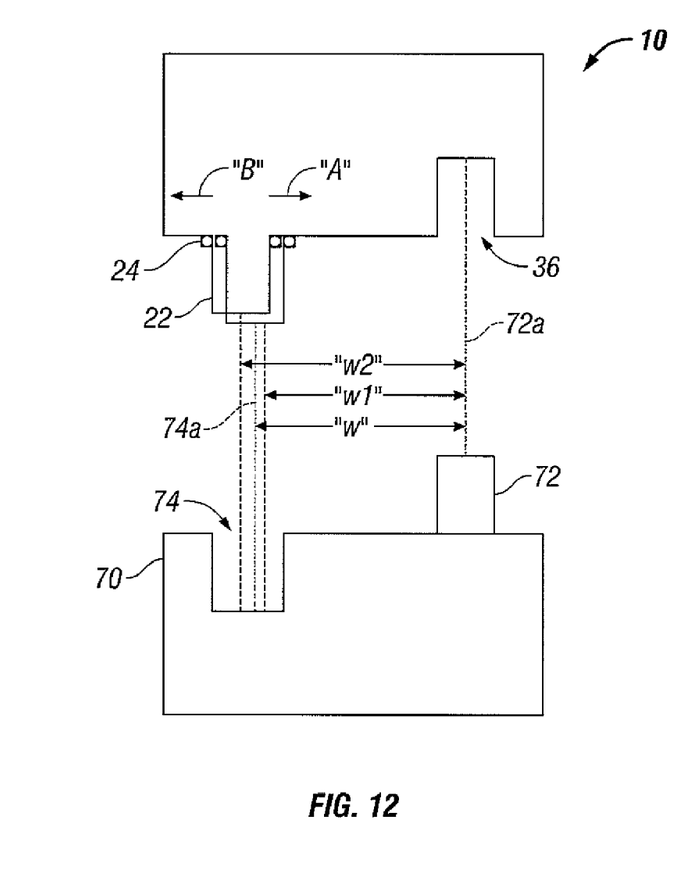
FIG. 12 is a schematic plan view of a receptacle assembly and a plug of an energy delivering device not aligned along a common central axis according to one embodiment of the present disclosure.
Figure 13:
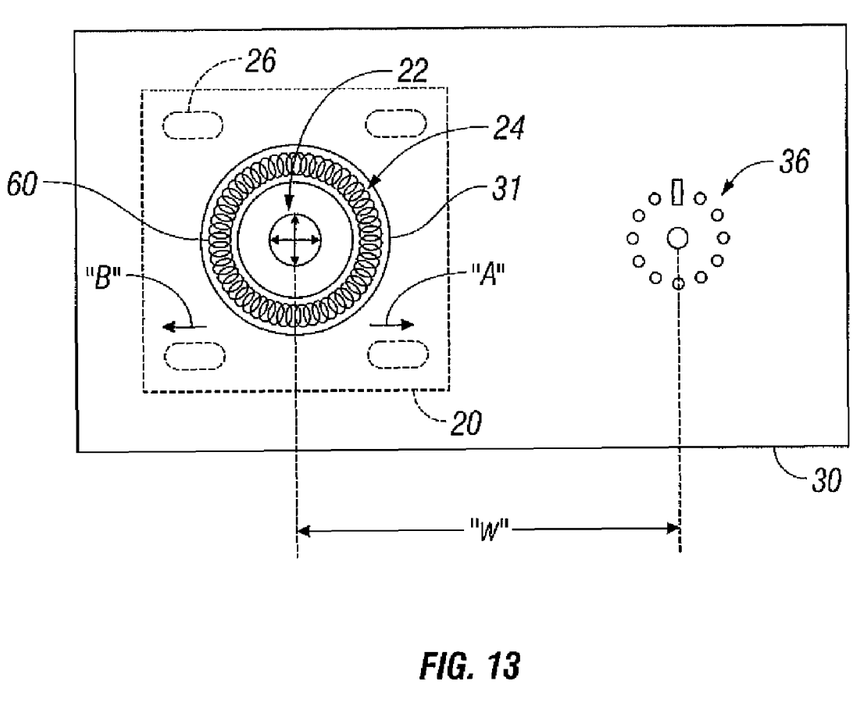
FIG. 13 is a schematic elevational view of the adapter plate assembly connected to the face plate, illustrating the operation thereof.

Turning now to FIGS. 11-13, a description of the operation of receptacle assembly 10 for connecting a plug 70 of an energy delivery device 50 is shown and described. As seen in FIG. 11, plug 70 includes a first terminal 72 configured for selective electromechanical connection with terminal 36 of receptacle assembly 10, and a second terminal 74 configured for selective electromechanical connection with terminal 22 of receptacle assembly 10. A central axis 72a of first terminal 72 is spaced a distance "W" from a central axis 74a of second terminal 74. During manufacturing of plug 70, distance "W" between first and second terminals 72 and 74 may vary from on energy delivery device 50 to another (e.g., distance "W" may be relatively greater or less from one energy device 50 to another).

Accordingly, during connection of plug 70 of energy device 50 to receptacle assembly 10 of energy source 40, adapter plate assembly 20 is movable relative to face plate 30 in order to compensate for or accommodate these differences in distance "W" between first and second terminals 72 and 74.

As seen in FIGS. 12 and 13, if a plug 70 including a first and second terminal 72 and 74, spaced a distance "W1" from one another (e.g., less than distance "W") is connected to receptacle assembly 10 of energy source 40, first terminal 72 is aligned and connected to terminal 36 of receptacle assembly 10 and, concomitantly therewith, terminal 22 is moved or urged in the direction of arrow "A" (compressing spacer member 24 at a first location therewith) until a central axis of terminal 22 is aligned with central axis 74a of second terminal 74, thereby allowing for proper connection of second terminal 74 with terminal 22.

Similarly, if a plug 70 including a first and second terminal 72 and 74, spaced a distance "W2" from one another (e.g., greater than distance "W") is connected to receptacle assembly 10 of energy source 40, first terminal 72 is aligned and connected to terminal 36 of receptacle assembly 10 and, concomitantly therewith, terminal 22 is moved or urged in the direction of arrow "B" (compressing spacer member 24 at a second location thereof) until a central axis of terminal 22 is aligned with central axis 74a of second terminal 74 thereby allowing for proper connection of second terminal 74, with terminal 22.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A receptacle assembly for use in connecting an energy source to an energy delivering device, the receptacle assembly comprising:
   a face plate defining an aperture having an inner surface;
   an adapter assembly including an adapter plate supporting a terminal, the adapter assembly including an annular flange extending from a surface of the adapter plate, the annular flange defining an outer surface and defining a central axis; and
   a spacer member interposed between the inner surface of the aperture of the face plate and the outer surface of the annular flange, wherein at least a portion of the spacer member is in operative communication with the inner surface of the face plate, wherein the spacer member permits omni-directional movement of the adapter plate and the terminal relative to the face plate such that the adapter plate and terminal are radially movable in a 360° direction relative to the central axis and the face plate.

2. The receptacle assembly according to claim 1, wherein the face plate and the adapter plate are adjustably coupled to each other.

3. The receptacle assembly according to claim 1, wherein the aperture of the face plate is configured to allow for omni-directional movement of the adapter plate, the aperture and the terminal being aligned along a common central axis.

4. The receptacle assembly according to claim 1, wherein the face plate is removably coupled to the energy source.

5. The receptacle assembly according to claim 1, wherein the face plate includes a connector that extends from a front surface of the face plate to a rear surface of the face plate.

6. The receptacle assembly according to claim 1, wherein the terminal is one of permanently coupled to the adapter plate and removably attached to the adapter plate.

7. The receptacle assembly according to claim 1, wherein the outer surface of the annular flange of the adapter plate includes an O-ring groove, and wherein the spacer member is an O-ring engaged with the O-ring grove.

8. The receptacle assembly according to claim 1, wherein the adapter plate includes at least two oversized apertures extending from a front surface of the adapter plate to a rear surface of the adapter plate, and wherein the face plate includes at least two apertures that correspond to the at least two oversized apertures, the at least two apertures each being configured to receive a fastening device.

9. The receptacle assembly according to claim 1, wherein the spacer member is resilient.

10. A receptacle assembly for use in connecting an energy source to an energy delivering device, the receptacle assembly comprising:
   a face plate defining an aperture having an inner surface the aperture is dimensioned to allow for omni-directional movement of the adapter plate;
   an adapter assembly including an adapter plate that is configured to support a terminal that is operatively connected to the energy source, the adapter assembly including an annular flange extending from a surface of the adapter plate, the annular flange defining an outer surface and defining a central axis; and
   a spacer member interposed between an inner surface of the aperture of the face plate and the outer surface of the annular flange, wherein at least a portion of the spacer contacts the inner surface of the face plate, wherein the spacer member permits omni-directional movement of at least one of the adapter plate and the terminal relative to the face plate such that the adapter plate and terminal are radially movable in a 360° direction relative to the central axis and the face plate.

11. The receptacle assembly according to claim 10, wherein the face plate and the adapter plate are adjustably coupled to each other.

12. The receptacle assembly according to claim 11, wherein the face plate includes a connector that extends from a front surface of the face plate to a rear surface of the face plate.

13. The receptacle assembly according to claim 10, wherein the terminal is one of permanently coupled to the adapter plate and removably attached to the adapter plate.

14. The receptacle assembly according to claim 10, wherein the outer surface of the annular flange of the adapter plate includes an O-ring groove, and wherein the spacer member is an O-ring engaged with the O-ring grove.

15. The receptacle assembly according to claim 10, wherein the adapter plate includes at least two oversized apertures extending from a front surface of the adapter plate to a rear surface of the adapter plate and the face plate includes at least two apertures that correspond to the at least two oversized apertures, the at least two apertures each being configured to receive a fastening device.

16. The receptacle assembly according to claim 10, wherein the spacer member is resilient.

17. A receptacle assembly for use in connecting an energy source to an energy delivering device, the receptacle assembly comprising:
   a face plate defining an aperture and a plane;
   an adapter assembly including an adapter plate configured to support a terminal that is operatively connected to the energy; and
   a spacer member operably disposed on the terminal, the spacer member interposed between a surface of the aperture of the face plate and a surface of the adapter plate, wherein the spacer member permits movement of at least one of the adapter plate and the terminal in a plane that is parallel to the plane defined by the face plate.

* * * * *